United States Patent [19]

Jorgensen

[11] 3,952,005

[45] Apr. 20, 1976

[54] 1-CARBOXYALKYL DERIVATIVES OF IMIDAZOLES

[75] Inventor: Dan Jorgensen, Virum, Denmark

[73] Assignee: A/S Dumex, Copenhagen, Denmark

[22] Filed: June 27, 1974

[21] Appl. No.: 483,826

[30] Foreign Application Priority Data

June 28, 1973 United Kingdom............... 30830/73
May 28, 1974 United Kingdom............... 23636/74

[52] U.S. Cl................................ 260/309; 424/273
[51] Int. Cl.$^2$........................................ C07D 233/60
[58] Field of Search.................................... 260/309

[56] References Cited

UNITED STATES PATENTS 3,784,691   1/1974   Fitzi et al............................ 260/309

FOREIGN PATENTS OR APPLICATIONS 3950M       2/1966    France................................ 260/309
1,458,080  10/1966    France................................ 260/309
1,538,154   7/1968    France................................ 260/309

OTHER PUBLICATIONS

Lettau Zeit. Chem. 1970, Vol. 10, Heft. 9, pp. 338–339.
Lettau Zeit. Chem. 1970. Vol. 10, Heft. 11, pp. 431–432.
Lettau Zeit. Chem. 1970. Vol. 10, Heft. 12, p. 462.
Lettau Zeit. Chem. 1971, Vol. 11, Heft. 1, pp. 10–11.
Birkofer et al. Chem. Abst. 1961, Vol. 55, columns 5484–5485.
Bogatkov et al. Chem. Abst. 1972, Vol. 76, No. 59525x.
Ellis et al. J. Pharm. Pharmacol. 1964, Vol. 16, pp. 400–407.
Sunjic et al. I Chem. Abst. 1969, Vol. 71, No. 90645.
Sunjic et al. II Chem. Abst. 1971, Vol. 74, No. 22763f.
Toth et al. Chem. Abst. 1968, Vol. 69, No. 96719q.
Easson et al. J. Chem. Soc. (London) 1932, pp. 1806–1812.

*Primary Examiner*—Natalie Trousof
*Attorney, Agent, or Firm*—Bacon & Thomas

[57] ABSTRACT

Imidazole derivatives substituted in the 1-position by a carboxyalkyl group or an ester of a such and the acid addition salts thereof, and where possible the alkali metal and alkaline earth metal salts thereof possess good antiphlogistic and analgesic activities. Such compounds are prepared, for example, by introducing the carboxyalkyl group or an ester of a such into the 1-position of a corresponding imidazole derivative unsubstituted in the 1-position. Alternatively such compounds are prepared by reacting an appropriate keto-oxime with an appropriate amino compound and an appropriate aldehyde or acetal and optionally reducing the imidazole derivative thus obtained.

2 Claims, No Drawings

1-CARBOXYALKYL DERIVATIVES OF IMIDAZOLES

The present invention relates to novel imidazole derivatives, the salts thereof and to processes for their preparation. The novel compounds possess interesting physiological properties.

According to one feature of the present invention there are provided compounds of the general formula:

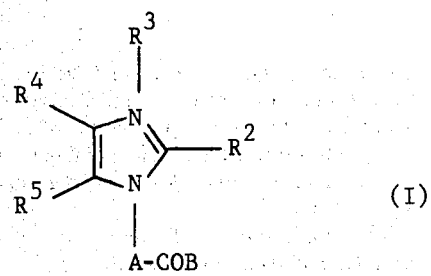

(wherein $R^2$, $R^4$ and $R^5$, which may be the same or different, each represents a hydrogen atom, a straight or branched alkyl group with 1–8 carbon atoms, a cycloalkyl group with 3–6 carbon atoms, or an optionally substituted phenyl group;

$R^3$ represents an oxygen atom or a lone pair;

A represents a —$CH_2$—, —$CH(CH_3)$— or —$CH_2CH_2$— group; and B represents an —OH or —OR group in which R represents a methyl or ethyl group), acid addition salts thereof, and (when B represents an —OH group) alkali metal and alkaline earth metal salts thereof.

Where $R^2$ and/or $R^4$ and/or $R^5$ represents an optionally substituted phenyl group, said phenyl group may, for example, be substituted by one, two or three atoms or groups, which atoms or groups may be the same or different, selected from the following; straight and branched alkyl and alkoxy groups with up to 4 carbon atoms per group; nitro, trifluoromethyl, hydroxy, amino and substituted amino groups and halogen atoms).

The compounds according to the present invention as hereinbefore defined may contain at least one asymmetric carbon atom and thus may exist not only in racemic form, but also in the form of optically active isomers. It will be appreciated that all such forms of the compounds of formula (I) (and salts thereof) are within the scope of the present invention.

The salts of the compounds of formula (I) according to the invention useful for incorporation in pharmaceutical compositions are physiologically compatible salts. Other salts may however be useful in the preparation of compounds of formula (I) and physiologically compatible salts thereof.

The compounds of general formula (I) and physiologically compatible salts thereof according to the present invention exhibit interesting physiological properties and in particular exhibit good antiphlogistic and analgesic activity.

The compounds of the present invention are exemplified by the following:

1-Carboxymethyl-2,4,5-triphenylimidazole and the acid addition, alkali metal and alkaline earth metal salts thereof;

1-Carboxymethyl-4,5-diphenylimidazole and the acid addition, alkali metal and alkaline earth metal salts thereof, preferably the sodium salt;

1-Carboxymethyl-2-(p-methoxyphenyl)-4,5-diphenylimidazole and the acid addition, alkali metal and alkaline earth metal salts thereof;

1-Carboxymethyl-2-isopropyl-4,5-bis(p-methoxyphenyl)-imidazole and the acid addition, alkali metal and alkaline earth metal salts thereof;

(±)1-(1-Carboxyethyl)-4,5-diphenylimidazole and the acid addition, alkali metal and alkaline earth metal salts thereof, preferably the sodium salt;

1-(2-Carboxyethyl)-2-isopropyl-4,5-diphenylimidazole and the acid addition, alkali metal and alkaline earth metal salts thereof;

1-(2-Carboxyethyl)-2-(p-chlorophenyl)-4,5-diphenylimidazole and the acid addition, alkali metal and alkaline earth metal salts thereof, preferably the sodium salt;

1-(2-Carboxyethyl)-2-isopropyl-4,5-diphenylimidazole-3-oxide and the acid addition, alkali metal and alkaline earth metal salts thereof;

1-(2-Carboxyethyl)-2-(p-chlorophenyl)-4,5-diphenylimidazole-3-oxide and the acid addition, alkali metal and alkaline earth metal salts thereof;

1-(2-Carboxyethyl)-2-(m-chlorophenyl)-4,5-diphenylimidazole-3-oxide and the acid addition, alkali metal and alkaline earth metal salts thereof;

1-(2-Carboxyethyl)-2-(2,4-dichlorophenyl)-4,5-diphenylimidazole-3-oxide and the acid addition, alkali metal and alkaline earth metal salts thereof;

1-(2-Carboxyethyl)-2-(p-chlorophenyl)-4-methyl-5-phenylimidazole-3-oxide and the acid addition, alkali metal and alkaline earth metal salts thereof;

1-(2-Carboxyethyl)-2-(p-chlorophenyl)-5-methyl-4-phenylimidazole-3-oxide and the acid addition, alkali metal and alkaline earth metal salts thereof;

1-(2-Carboxyethyl)-2-(p-chlorophenyl)-4,5-bis-(p-methoxyphenyl)-imidazole-3-oxide and the acid addition, alkali metal and alkaline earth metal salts thereof;

1-(2-Carboxyethyl)-2-(p-methoxyphenyl)-4,5-diphenylimidazole-3-oxide and the acid addition, alkali metal and alkaline earth metal salts thereof;

1-(2-Carboxyethyl)-2-(p-toluyl)-4,5-diphenylimidazole-3-oxide and the acid addition, alkali metal and alkaline earth metal salts thereof;

1-Carboxymethyl-2-(p-nitrophenyl)-4,5-diphenylimidazole-3-oxide and the acid addition, alkali metal and alkaline earth metal salts thereof;

1-(2-Carboxyethyl)-2-ethyl-4,5-bis-(p-methoxyphenyl)-imidazole-3-oxide and the acid addition, alkali metal and alkaline earth metal salts thereof;

1-(2-Carboxyethyl)-2-isopropyl-4,5-bis-(p-methoxyphenyl)-imidazole-3-oxide and the acid addition, alkali metal and alkaline earth metal salts thereof;

1-Carboxymethyl-2-isopropyl-4,5-bis-(p-methoxyphenyl)-imidazole-3-oxide and the acid addition, alkali metal and alkaline earth metal salts thereof;

1-(1-Carboxyethyl)-2,4,5-triphenylimidazole-3-oxide and the acid addition, alkali metal and alkaline earth metal salts thereof;

(S)-1-(1-Carboxyethyl)-2-isopropyl-4,5-diphenylimidazole-3-oxide and acid addition, alkali metal and alkaline earth metal salts thereof;

1-(2-Carboxyethyl)-2-cyclohexyl-4,5-diphenylimidazole-3-oxide and acid addition, alkali metal and alkaline earth metal salts thereof;

1-(2-Carboxyethyl)-2-isopropyl-4,5-diphenylimidazole and acid addition, alkali metal and alkaline earth metal salts thereof, preferably the hydrochloride;

1-(2-Carboxyethyl)-2-(3,4-dichlorophenyl)-4,5-diphenylimidazole and acid addition, alkali metal and alkaline earth metal salts thereof;

1-(2-Carboxyethyl)-2-(p-chlorophenyl)-4,5-bis-(p-methoxyphenyl)-imidazole and acid addition, alkali metal and alkaline earth metal salts thereof;

1-(2-Carboxyethyl)-2-(p-methoxyphenyl)-4,5-diphenylimidazole and acid addition, alkali metal and alkaline earth metal salts thereof;

1-(2-Carboxyethyl)-2-isopropyl-4,5-bis-(p-methoxyphenyl)-imidazole and acid addition, alkali metal and alkaline earth metal salts thereof;

1-(1-Carboxyethyl)-2,4,5-triphenylimidazole and acid addition, alkali metal and alkaline earth metal salts thereof.

Preferred compounds according to the present invention, by virtue of their favourable physiological activity, include the following:

1-(2-carboxyethyl)-2-(p-chlorophenyl)-4,5-bis-(p-methoxyphenyl)-imidazole, the acid addition, alkali metal and alkaline earth metal salts thereof;

1-carboxymethyl-2-isopropyl-4,5-bis-(p-methoxyphenyl)-imidazole, the acid addition, alkali metal and alkaline earth metal salts thereof;

1-(2-carboxyethyl)-2-isopropyl-4,5-diphenylimidazole, the acid addition, alkali metal and alkaline earth metal salts thereof;

1-(2-(carboxyethyl)-2-(p-chlorophenyl)-4,5-diphenyl-imidazole, the acid addition, alkali metal (e.g. sodium) and alkaline earth metal salts thereof; and 1-(2-carboxyethyl)-2-(p-toluyl)-4,5-diphenyl-imidazole-3-oxide, the acid addition, alkali metal and alkaline earth metal salts thereof.

Especially preferred compounds according to the present invention, by virtue of their especially favourable physiological activity, are:

1-(2-carboxyethyl)-2-isopropyl-4,5-bis(p-methoxyphenyl)-imidazole the acid addition, alkali metal and alkaline earth salts thereof.

The compounds of formula (I) may, for example, be synthesised via the corresponding imidazole derivative without the side chain in the 1-position of the imidazole ring, i.e. compounds of formula (II) (wherein $R^2$, $R^3$, $R^4$ and $R^5$ are as hereinbefore defined).

According to a further feature of the present invention there is thus provided a process for the preparation of compounds of formula (I) as hereinbefore defined (in which B represents an —OR group as hereinbefore defined) which comprises reacting a compound of the formula:

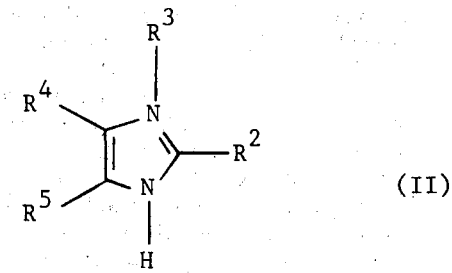

(II)

(wherein $R^2$, $R^3$, $R^4$ and $R^5$ are as hereinbefore defined) with a compound of the formula:

(wherein A and R are as hereinbefore defined and X represents an atom or group removable as an anion) whereby a compound of formula (I) is obtained.

A compound of formula (III) is preferably used in which X represents a halogen atom e.g. a chlorine or bromine atom.

The compound of formula (II) is advantageously dissolved or suspended in an appropriate solvent e.g. dimethylformamide, dimethylacetamide, toluene, ethanol or acetone, and an alkaline condensing agent e.g. sodium hydride, sodium ethoxide or potassium carbonate, may also be conveniently added. The reaction is advantageously effected at an elevated temperature e.g. from 30°C to 110°C for an appropriate period e.g. from 6 to 72 hours. If required the compound of formula (I) in which B represents an alkoxy group with 1 to 2 carbon atoms, thus formed, may be converted into a compound of formula (I) in which B represents an —OH group.

Imidazoles of formula (II) may, for example, be prepared according to methods known per se; see, for example, Davidson, Weiss and Jelling: *J. Org. Chem.* 2 (1937) 328, or H. Bredereck, R. Gompper and D. Hayer; Ber. 92 (1959) 338, or *H. Lettau: Z. Chem.* 11 (1971) 10.

According to a further feature of the present invention there is provided a process for the preparation of compounds of formula (I) as hereinbefore defined (wherein B represents an —OH group) which comprises hydrolysing a compound of the formula:

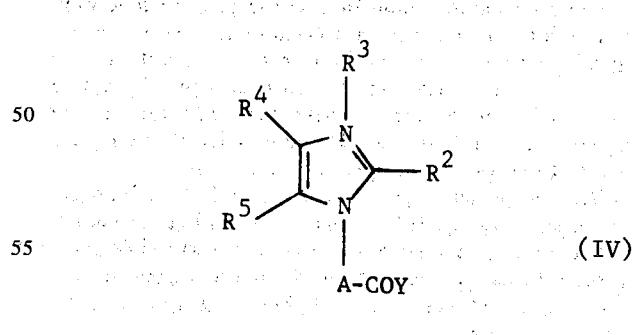

(IV)

(wherein Y represents a hydrolytically removable atom or group and $R^2$, $R^3$, $R^4$ and $R^5$ are as hereinbefore defined). Thus compounds of the formula (IV) may be used in which Y represents an alkoxy group e.g. with 1 to 2 carbon atoms. The hydrolysis may, for example, be effected by alkaline hydrolysis.

The preparation of the compounds of formula (I) in which A represents a —CH$_2$CH$_2$— group and B represents an —OH group is most favourably effected by acid hydrolysis of the corresponding ester, since to some extent the whole side chain in the 1-position of the imidazole ring is split off by alkaline hydrolysis.

According to a further feature of the present invention there is provided a process for the preparation of compounds of formula (I) as hereinbefore defined (in which A represents a —CH$_2$CH$_2$— group and B represents an —OH group) which comprises subjecting a compound of formula (II) to cyanoethylation and subsequently converting the compound thus obtained into a compound of formula (I) by acid hydrolysis.

According to a further feature of the present invention there is provided a process for the preparation of compounds of formula I as hereinbefore defined (wherein R$^2$ is other than a hydrogen atom and R$^3$ represents a lone pair with the proviso that R$^4$ and R$^5$ do not both represent hydrogen atoms) which comprises reducing a compound of the formula

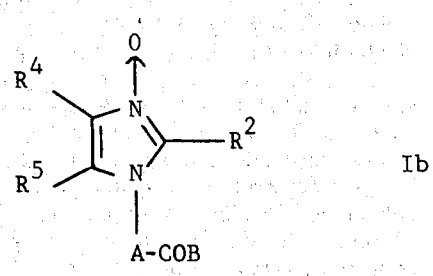

Ib (wherein R$^2$, R$^4$, R$^5$, A and B are as hereinbefore defined) whereby the desired compound of formula I is obtained. The reduction is preferably effected by the use of zinc in acetic acid.

The present invention also provides a process for the preparation of compounds of formula I as hereinbefore defined (wherein R$^2$ represents a hydrogen atom, and R$^3$ represents a lone pair with the proviso that R$^4$ and R$^5$ do not both represent hydrogen atoms) which comprises desulfurizing a compound of the formula:

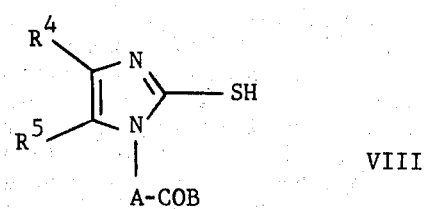

VIII (wherein A, B, R$^4$ and R$^5$ are as hereinbefore defined with the proviso that R$^4$ and R$^5$ do not both represent hydrogen atoms). The desulfurization is preferably effected in the presence of Raney nickel. The compound of formula VIII is preferably first prepared by reacting a compound of formula:

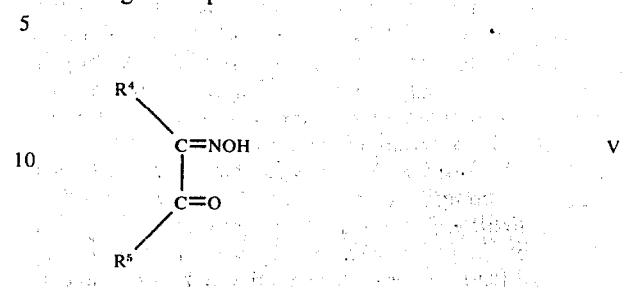

V (wherein R$^4$ and R$^5$ are as hereinbefore defined with the proviso that R$^4$ and R$^5$ do not both represent hydrogen atoms) with a compound of the formula:

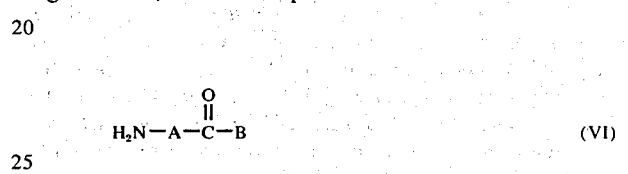

(VI)

(wherein A and B are as hereinbefore defined) and with formaldehyde in the presence of hydrogen sulphide. The reaction is desirably effected at an elevated temperature and conveniently in the presence of an appropriate solvent.

According to a still further feature of the present invention there is provided a process for the preparation of compounds of formula I as hereinbefore defined (wherein R$^2$ is other than hydrogen, and R$^3$ represents an oxygen atom with the proviso that R$^4$ and R$^5$ do not both represent hydrogen atoms) which comprises reacting a compound of the formula:

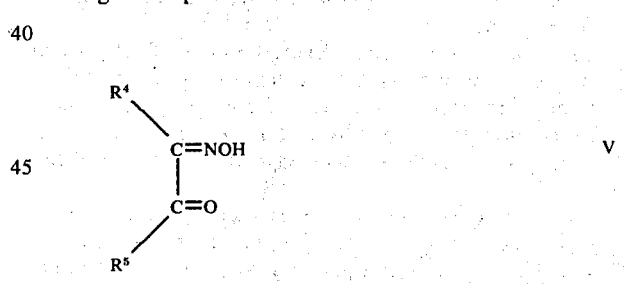

V (wherein R$^4$ and R$^5$ are as hereinbefore defined with the proviso that R$^4$ and R$^5$ do not both represent hydrogen atoms) with a compound of the formula

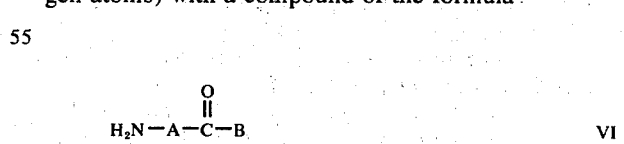

VI (wherein A and B are as hereinbefore defined) and with a compound of the formula:

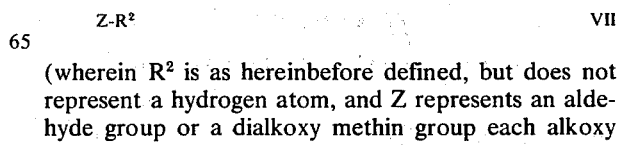

VII (wherein R$^2$ is as hereinbefore defined, but does not represent a hydrogen atom, and Z represents an aldehyde group or a dialkoxy methin group each alkoxy group containing 1 or 2 carbon atoms).

According to a yet still further feature of the present invention there is provided a process for the production of a compound of formula I (wherein $R^2$ is other than a hydrogen atom and $R^3$ represents a lone pair with the proviso that $R^4$ and $R^5$ do not both represent hydrogen atoms) which comprises reacting a compound of formula V (as hereinbefore defined) with a compound of formula VI (as hereinbefore defined) and with a compound of formula VII (as hereinbefore defined) whereby a compound of formula I (wherein $R^2$ is other than a hydrogen atom and $R^3$ represents an oxygen atom with the proviso that $R^4$ and $R^5$ do not both represent hydrogen atoms) is obtained which compound is subsequently reduced whereby a compound of formula I (wherein $R^2$ is other than a hydrogen atom and $R^3$ represents a lone pair with the proviso that $R^4$ and $R^5$ do not both represent hydrogen atoms) is obtained.

The latter two processes are preferably effected by the use of a compound of formula V in which $R^4$ and $R^5$, which may be the same or different, each represents an optionally substituted phenyl group. Where, however, a compound of formula VII is used in which $R^2$ represents an alkyl group a compound of formula VII is preferably used in which Z represents a dialkoxy methin group. The reaction is advantageously effected in an appropriate solvent e.g. acetic acid, ethanol, butanol or dimethylformamide.

The compounds of formula (I) (in which B represents —OMe or —$OC_2H_5$) can be prepared by refluxing compounds of formula (I) (in which B represents —OH) in absolute methanol or ethanol containing hydrogen chloride.

According to a still further feature of the present invention there are provided pharmaceutical compositions comprising as active ingredient at least one compound of formula (I) or a physiologically compatible salt thereof in association with a pharmaceutical carrier or excipient.

According to a yet still further feature of the present invention there are provided veterinary compositions comprising as active ingredient at least one compound of formula (I) or a physiologically compatible salt thereof in association with a veterinary carrier or excipient.

The compositions may be presented in a form suitable for oral, topical, rectal or parenteral administration. Thus, for example, the compositions may be solid or liquid and may take the form of granules, tablets, coated tablets, capsules, syrups, suppositories, ointments, creams, emulsions, suspensions, drops or injectable solutions, such compositions comprising carriers or excipients conventionally used in the pharmaceutical and veterinary art.

Advantageously, the compositions may be formulated as dosage units, each unit being adapted to supply a fixed dose of active ingredient. Tablets, coated tablets and capsules are examples of suitable dosage unit forms. Each dosage unit preferably contains 2 to 100 mg of active ingredient.

The following examples illustrate the preparation of compounds according to the invention:

EXAMPLE 1

1-carboxymethyl-2,4,5-triphenylimidazole 59.2 g (0.2 mole) Of 2,4,5-triphenylimidazole are added, with stirring, to a cooled slurry of 6 g (0.25 mole) of sodium hydride in 120 ml. of dimethylacetamide, 35 g (0.21 mole) of ethyl bromoacetate are then added dropwise and the reaction mixture is stirred for 72 hours at 30° C. The mixture is cooled in an ice bath, and a solution of 40 g of sodium hydroxide in 400 ml. of water is carefully added. The mixture is heated on a steam bath for 6 hours. After cooling, 1000 ml of water are added and the pH is adjusted to 1 by means of 6N hydrochloric acid. The precipitate which forms is filtered off and dissolved in 1500 ml. of 2N sodium hydroxide. A turbidity consisting of unreacted starting material is removed by filtering through celite. The filtrate is extracted with 3 × 300 ml. of benzene, and 6N hydrochloric acid is then added until a pH of 1 is reached. The precipitated formed is filtered off and dried. Melting point: 291.6° C.

Thin layer chromatography reveals one spot only and the $R_f$-value of this is different from that of the starting material.

Equivalent weight found by perchloric acid titration: 391.7. Equivalent weight calculated for 1-carboxymethyl-2,4,5-triphenylimidazole: 390.87.

EXAMPLE 2

Sodium 1-carboxymethyl-4,5-diphenylimidazole 2.3 g (0.1 equivalent) Of sodium and then 22 g. (0.1 mol) of 4,5-diphenylimidazole are dissolved in 350 ml of absolute ethanol. The solution is heated to reflux temperature and 16.7 g (0.1 mol) of ethyl bromoacetate are added dropwise for 30 minutes. The reflux is continued for 16 hours. After cooling, the precipitate (sodium bromide) is filtered off and discarded. The filtrate is evaporated to half the volume, 150 ml. of 20% aqueous sodium hydroxide are added and the mixture is heated for 4 hours on a steam bath. The ethanol is evaporated in vacuo, and 1000 ml. of 0.5N sodium hydroxide are added to the residue. From this suspension unreacted starting material is removed by extraction with ether. After the ether extraction the water phase is evaporated to ¼ its volume and the precipitate which forms is filtered off, washed with a little water, and dried overnight at 105° C.

Thin layer chromatography reveals one spot only and the $R_f$-value of this is different from that of the starting material.

Equivalent weight found by titration with 0.1N HCl: 304.26. Equivalent weight calculated for Na-salt of 1-carboxymethyl-4,5-diphenylimidazole: 306.39.

EXAMPLE 3

1-Carboxymethyl-2-(p-methoxyphenyl)-4,5-diphenylimidazole 65.2g (0.20 mole) Of 2-(p-methoxyphenyl)-4.5-diphenylimidazole are added with stirring to a cooled slurry of 6.5 g (0.27 mol) of sodium hydride in 250 ml. of dimethylformamide. A solution of 24.5 g (0.20 mol) of ethyl chloroacetate in 100 ml of dimethylformamide is added dropwise, over a period of 15 minutes, and the mixture is then heated to 100° C for 4½ hours. After cooling, 250 ml of 1N sodium hydroxide is added and the mixture is heated on a steam bath for 4 hours. After cooling the suspension is filtered and the filter cake is washed with a little water. It is then suspended in 750 ml. of 0.5N sodium hydroxide and extracted with ether in order to remove unreacted starting material. The pH is adjusted to 4.5 with 4N hydrochloric acid and the precipitate is filtered off, washed with a little water and dried. Melting point: above 275° C.

Thin layer chromatography reveals one spot only and the $R_f$-value of this is different from that of the starting material.

Equivalent weight found by titration with 0.1N sodium hydroxide: 387.19. Equivalent weight calculated for 1-carboxymethyl-2-(p-methoxyphenyl)-4,5-diphenylimidazole: 384.42.

EXAMPLE 4

1-Carboxymethyl-2-isopropyl-4,5-bis-(p-methoxyphenyl)-imidazole 3.8 g (0.165 mol) Of sodium and then 49 g (0.15 mole) of 2-isopropyl-4,5-bis(p-methoxyphenyl)-imidazole are dissolved in 525 ml. of absolute ethanol. The solution is heated to reflux temperature and 18.7 ml (0.165 mole) of ethyl bromoacetate is added dropwise thereto over a period of 30 minutes. The reflux is continued for 24 hours whereafter half of the alcohol is evaporated. 225 ml Of 20% aqueous sodium hydroxide are added and the reaction mixture is heated on a steam bath for 4 hours. A precipitate of unreacted stating material is filtered off and, after evaporation of the remaining ethanol, the filtrate is extracted with ether to remove further unreacted starting material. Half-concentrated hydrochloric acid is then added until a pH of 4.5 is achieved, and the mixture is evaporated to dryness. The residue is dried over phosphorus pentoxide and extracted with absolute ethanol. By evaporation of the alcohol extract, a white compound is obtained which by thin layer chromatography proves to have a $R_f$-value different from that of the starting material.

Equivalent weight found by titration with 0.1N sodium hydroxide: 382.69. Equivalent weight calculated for 1-carboxymethyl-2-isopropyl-4,5-bis(p-methoxyphenyl)-imidazole: 380.43.

EXAMPLE 5

Sodium salt of (±) 1-(1-carboxyethyl)-4,5-diphenylimidazole 3.8 g (0.165 mol) Of sodium and then 33g (0.15 mole) of 4,5-diphenylimidazole are dissolved in 525 ml. of absolute ethanol. The solution is heated to reflux and 21.5 ml (0.165 mole) of ethyl alpha-bromopropionate are added dropwise over a period of 30 minutes. The reflux is continued for 24 hours whereafter half of the alcohol is evaporated. 225 ml. Of 20% aqueous sodium hydroxide are added and the reaction mixture is allowed to stand on a steam bath for 4 hours. After evaporation of the remaining ethanol, the resulting suspension is extracted with ether to remove unreacted starting material. Finally the precipitate is filtered off, washed with a little water and dried in vacuo at 105° C.

This layer chromatography reveals a $R_f$-value different from that of the starting material.

Equivalent weight found by titration with 0.1N HCl: 317. Equivalent weight calculated for the sodium salt of (±)1-(1-carboxyethyl)-4,5-diphenylimidazole: 314.32.

EXAMPLE 6

1-(2-carboxyethyl)-2-isopropyl-4,5-diphenylimidazole

In 150 ml. of pyridine 1.4 g (0.02 mol) of sodium ethoxide and 26.2 g (0.1 mole) of 2-isopropyl-4,5-diphenylimidazole are dissolved. 13.2 ml (0.2 mole) Of acrylonitrile are then added over a period of 30 minutes. The mixture is stirred at room temperature for 24 hours and is then poured out into 1 liter of water. The precipitate is filtered off, washed with water and then refluxed in 150 ml of half-concentrated sulphuric acid for 6 hours. After cooling, the sulphuric acid solution is slowly added dropwise to 500 ml. of 20% aqueous sodium hydroxide. The precipitate is filtered off and dried. To remove unreacted starting material, it is extracted with 4 × 200 ml of chloroform. The residue is dried again and extracted with 2 × 200 ml of hot absolute ethanol. After evaporation of the ethanol extract, the residue is suspended in a little water and 4N sulphuric acid is added until a pH of 4.5 is achieved. The precipitate is filtered off and washed with a very little water and dried. Melting point: 213°–220° C.

Thin layer chromatography reveals a $R_f$-value different from that of the starting material.

Equivalent weight found by titration with 0.1N NaOH: 328.17. Equivalent weight calculated for 1-(2-carboxyethyl)-2-isopropyl-4,5-diphenylimidazole: 334.41.

EXAMPLE 7

Sodium salt of 1-(2-carboxyethyl)-2-(p-chlorophenyl)-4,5-diphenylimidazole 0.92 g (0.0135 mole) Of sodium ethoxide and 14.2 g (0.043 mole) of 2-(p-chlorophenyl)-4,5-diphenylimidazole are dissolved in 65 ml of pyridine. 5.7 ml. (0.085 mole) Of acrylonitrile are added dropwise over a period of 30 minutes. The mixture is stirred at room temperature for 24 hours and is then poured out into 1 liter of water. The precipitate is filtered off, washed with water and refluxed in 85 ml of half-concentrated sulphuric acid for 6 hours. After cooling, the precipitate is filtered off, suspended in 400 ml of 2N sodium hydroxide and extracted with ether to remove unreacted starting material. Finally the precipitate is filtered off, washed with a little water and dried.

Thin layer chromatography reveals a $R_f$-value different from that of the starting material.

Equivalent weight found by titration with 0.1N HCl: 419.93. Equivalent weight calculated for the sodium salt of 1-(2-carboxyethyl)-2-(p-chlorophenyl)-4,5-diphenylimidazole: 424.86.

EXAMPLE 8

1-(2-carboxyethyl)-2-isopropyl-4,5-diphenylimidazole-3-oxide

In 200 ml of glacial acetic acid 5.25 ml (0.1 mole) of isobutyraldehyde, 22.5 g (0.1 mole) of benzil monoxime and 8.9 g (0.1 mole) of beta-alanine is heated to reflux temperature for 3 hours. After cooling the mixture is added dropwise under vigorous stirring to one litre of concentrated aqueous ammonia. The solution is extracted with several portions of ether which is discarded. Now pH is adjusted to 7–8 by addition of hydrochloric acid, and further extractions with ether are performed on the resulting slurry. Also this ether is discarded. Finally pH is adjusted to 3 by further addition of hydrochloric acid and the precipitate is filtered off, washed with water and dried. Melting point: 245°–250° C. Thin layer chromatography reveals one spot only.

Equivalent weight found by titration with perchloric acid: 358.4. Equivalent weight calculated for 1-(2-carboxyethyl)-2-isopropyl-4,5-diphenylimidazole-3-oxide: 350.41.

IR- and $^1$H-NMR-spectra recorded were found to conform to the proposed structure of the reaction product.

Similarly prepared were the following compounds:
a. 1-(2-carboxyethyl)-2-(p-chlorophenyl)-4,5-diphenylimidazole-3-oxide, melting point 240–243° C (dec.), from 22.5 g (0.1 mole) of benzil monoxime, 8.9 g (0.1 mole) of beta-alanine and 14 g (0.1 mole) of p-chlorobenzaldehyde.
b. 1-(2-carboxyethyl)-2-(m-chlorophenyl)-4,5-diphenylimidazole-3-oxide, melting point 232°–234° C (dec), from 22.5 g (0.1 mole) of benzil monoxime; 8.9 g (0.1 mole) of beta-alanine and 14.0 g (0.1 mole) of m-chlorobenzaldehyde.
c. 1-(2-carboxyethyl)-2-(2,4-dichlorophenyl)-4,5-diphenylimidazole-3-oxide, melting point 229°–231°C (dec.), from 22.5 g (0.1 mol) of benzil monoxime; 8.9 g (0.1 mole) of beta-alanine and 21 g. (0.12 mole) of 2,4-dichlorobenzaldehyde.
d. 1-(2-carboxyethyl)-2-(p-chlorophenyl)-4-methyl-5-phenylimidazole-3-oxide, melting point 156°–158° C, from 16.3 g (0.1 mole) of alpha-hydroximinopropiophenone; 8.9 g (0.1 mole) of beta-alanine and 14.0 g (0.1 mole) of p-chlorobenzaldehyde.
e. 1-(2-carboxyethyl)-2-(p-chlorophenyl)-5-methyl-4-phenylimidazole-3-oxide, melting point 203°–206° C, from 16.3 g (0.1 mole) of 1-hydroximino-1-phenyl-2-propanone; 8.9 g (0.1 mole) of beta-alanine and 14.0 g (0.1 mole) of p-chlorobenzaldehyde.
f. 1-(2-carboxyethyl)-2-(p-chlorophenyl)-4,5-bis-(p-methoxyphenyl)-imidazole-3-oxide, melting point 236° C (dec.), from 28.5 g (0.1 mole) of anisil monoxime; 8.9 g (0.1 mole) of beta-alanine and 14.9 g (0.1 mole) of p-chlorobenzaldehyde.
g. 1-(2-carboxyethyl)-2-(p-methoxyphenyl)-4,5-diphenylimidazole-3-oxide, melting point 196°–202° C from 22.5 g (0.1 mole) of benzil monoxime; 8.9 g (0.1 mole) of beta-alanine and 13.6 g (0.1 mole) of anisaldehyde.
h. 1-(2-carboxyethyl)-2-(p-toluyl)-4,5-diphenylimidazole-3-oxide, melting point 214°–216° C, from 22.5 g (0.1 mole) of benzil monoxime; 8.9 g (0.1 mole) of beta alanine and 12.0 g (0.1 mole) of p-toluylaldehyde.
i. 1-carboxymethyl-2-(p-nitrophenyl)-4,5-diphenylimidazole-3-oxide, melting point 250°–253° C, from 22.5 g (0.1 mole) of benzil monoxime; 7.5 g (0.1 mole) of glycine and 15.1 g (0.1 mole) of p-nitrobenzaldehyde.
j. 1-(2-carboxyethyl)-2-ethyl-4,5-bis-(p-methoxyphenyl)- imidazole-3-oxide, melting point 231°–233° C, from 28.5 g (0.1 mole) of anisil monoxime; 8.9 g (0.1 mole) of beta-alanine and 11 ml. (0.15 mole) of propionaldehyde.
k. 1-(2-carboxyethyl)-2-isopropyl-4,5-bis-(p-methoxyphenyl)-imidazole-3-oxide, melting point 240°–242° C from 28.5 g (0.1 mole) of anisil monoxime; 8.9 g (0.1 mole) of beta-alanine and 7.3 g (0.1 mole) of isobutyraldehyde.
l. 1-carboxymethyl-2-isopropyl-4,5-bis-(p-methoxyphenyl)-imidazole-3-oxide, melting point 254°–258° C from 28.5 g (0.1 mole) of anisil monoxime, 7.5 g (0.1 mole) of glycine and 7.3 g (0.1 mole) of isobutyraldehyde.
m. 1-(1-carboxyethyl)-2,4,5-triphenylimidazole-3-oxide, melting point 260°–263° C from 22.5 g (0.1 mole) of benzil monoxime, 8.9 g (0.1 mole) of d,l-alanine and 10.6 g (0.1 mole) of benzaldehyde.
n. (S)-1-(1-carboxyethyl)-2-isopropyl-4,5-diphenylimidazole-3-oxide, melting point 240°–243° C, from 22.5 g (0.1 mole) of benzil monoxime, 8.9 g (0.1 mole) of L-alanine and 7.3 g (0.1 mole) of isobutyraldehyde.
o. 1-(2-carboxyethyl)-2-cyclohexyl-4,5-diphenylimidaozle-3-oxide, melting point 240°–243° C, from 22.5 g (0.1 mole) of benzil monoxime, 8.9 g (0.1 mole) of β-alanine and 11.2 g (0.1 mole) of cyclohexylaldehyde.

EXAMPLE 9

1-(2-carboxyethyl)-2-isopropyl-4,5-diphenylimidazole-HCl

In 200 ml, of glacial acetic acid 5.25 ml (0.1 mole) of isobutyraldehyde, 22.5 g (0.1 mole) of benzil monoxime and 8.9 g (0.1 mole) of beta-alanine is heated to reflux temperature for 3 hours. Then 20 g. of zinc powder is added to the refluxing mixture, and refluxing is continued for further 3 hours. After cooling the precipitate of zinc acetate is filtered off and discarded. The filtrate is added dropwise under vigorous stirring to one litre of concentrated aqueous ammonia. The slurry is extracted with ether which is discarded. Now pH is adjusted to 7–8 by addition of hydrochloric acid, and further extractions with ether are performed on the slurry. Also this ether is discarded. Finally pH is adjusted to 2 by further addition of hydrochloric acid and the precipitate is filtered off, washed with water and dried. Melting point: 236°–240° C. Thin layer chromatography reveals one spot only.

Equivalent weight found by titration with 0.1N NaOH; 381.3, and by titration with 0.05N AgNO$_3$: 379.4. Equivalent weight calculated for 1-(2-carboxyethyl)-2-isopropyl-4,5-diphenylimidazole hydrochloride: 370.87.

IR- and $^1$H-NMR-spectra recorded were found to conform to the proposed structure of the reaction product.

Similarly prepared were the following compounds:
a. 1-(2-carboxyethyl)-2-(p-chlorophenyl)-4,5-diphenylimidazole, melting point 222°–225° C, from 22.5 g (0.1 mole) of benzil monoxime, 8.9 g (0.1 mole) of beta-alanine, 14.0 g (0.1 mole) of p-chlorobenzaldehyde and 20 g of zinc powder.
b. 1-(2-carboxyethyl)-2-(3,4-dichlorophenyl)-4,5-diphenylimidazole, melting point 224°C, from 22.5 g (0.1 mole) of benzil monoxime, 8.9 g (0.1 mole) of beta-alanine, 21 g. (0.12 mole) of 3,4-dichlorobenzaldehyde and 20 g of zinc powder.
c. 1-(2-carboxyethyl)-2-(p-chlorophenyl)-4,5-bis-(p-methoxyphenyl)-imidazole, melting point 249°–251° C from 28.5 g (0.1 mole) of anisil monoxime, 8.9 g (0.1 mole) of beta alanine and 20 g of zinc powder.
d. 1-(2-carboxyethyl)-2-(p-methoxyphenyl)-4,5-diphenylimidazole, melting point 168°–69° C, from 22.5 g, (0.1 mole) of benzil monoxime, 8.9 g (0.1 mole) of beta-alanine and 20 g of zinc powder.
e. 1-(2-carboxyethyl)-2-isopropyl-4,5-bis-(p-methoxyphenyl)-imidazole, melting point 231°–233° C, from 28.5 g (0.1 mole) of anisil monoxime, 8.9 g (0.1 mole) of beta-alanine, 7.3 g (0.1 mole) of isobutyraldehyde and 20 g. of zinc powder.

f. 1-(1-carboxyethyl)-2,4,5-triphenylimidazole, melting point 228°–230° C, from 22.5 g (0.1 mole) of benzil monoxime, 8.9 g (0.1 mole) of DL -alanine, 10.6 g (0.1 mole) of benzaldehyde and 20 g. of zinc powder.

EXAMPLE 10

1-(2-carboxyethyl)-2-(p-chlorophenyl)-4,5-diphenylimidazole-3-oxide

In 20 ml. of butanol 2.25 g (0.01 mole) of benzil monoxime, 0.9 g (0.01 mole) of beta-alanine and 1.4 g (0.01 mole) of p-chlorobenzaldehyde are suspended or dissolved. The mixture is heated to reflux for 3 hours and after cooling the precipitate is filtered off, washed with a little butanol and dried. Melting point: 238°–241° C. By thin layer chromatography, IR- and $^1$H-NMR-spectroscopy the compound proved to be identical with an authentic sample of 1-(2-carboxyethyl)-2-(p-chlorophenyl)-4,5-diphenylimidazole-3-oxide.

I claim:
1. A compound of the formula

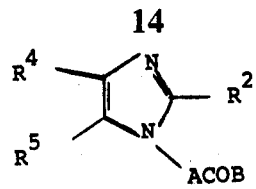

wherein $R^2$ represents hydrogen, straight or branched alkyl of 1–3 carbon atoms, cycloalkyl of 3–6 carbon atoms or phenyl optionally substituted by at least one member of the group consisting of chlorine, methyl, methoxy and nitro, and $R^4$ and $R^5$ which may be the same or different, each represent phenyl or p-methoxyphenyl; A represents —CH$_2$—, —CH(CH$_3$)—or —CH$_2$CH$_2$—and B represents —OH or —OR in which R is selected from the group consisting of methyl and ethyl groups; physiologically compatable acid addition salts thereof, and when B represents an —OH group, physiologically compatable alkali metal and alkaline earth metal salts thereof.

2. A compound of claim 1 selected from the group consisting of:
1-Carboxymethyl-2-isopropyl-4,5-bis (p-methoxyphenyl)-imidazole and the acid addition, alkali metal and alkaline earth metal salts thereof;
1-(2-Carboxyethyl)-2-isopropyl-4,5-diphenylimidazole and the acid addition, alkali metal and alkaline earth metal salts thereof;
1-(2-Carboxyethyl)-2-isopropyl-4,5-bis-(p-methoxyphenyl)-imidazole and the acid addition, alkali metal and alkaline earth metal salts thereof.

* * * * *